(12) United States Patent
Garlick et al.

(10) Patent No.: US 6,590,830 B1
(45) Date of Patent: Jul. 8, 2003

(54) APPARATUS AND PROCESS MODIFICATIONS IN ULTRASONIC HOLOGRAPHY TO IMPROVE IMAGE QUALITY

(75) Inventors: George F. Garlick, Richland, WA (US); Ronald L. Shelby, Richland, WA (US); Jerod O. Shelby, Richland, WA (US)

(73) Assignee: Advanced Imaging Technologies, Inc., Preston, WA (US)

( * ) Notice: Subject to any disclaimer, the term of this patent is extended or adjusted under 35 U.S.C. 154(b) by 50 days.

(21) Appl. No.: 09/589,855

(22) Filed: Jun. 8, 2000

(51) Int. Cl.$^7$ .................... G01N 29/04; G03H 3/00
(52) U.S. Cl. .................. 367/8; 73/603; 73/605; 359/901; 600/437
(58) Field of Search .............. 367/7, 8, 10; 73/603, 73/605; 359/9, 901; 600/437

(56) References Cited

U.S. PATENT DOCUMENTS

| | | | |
|---|---|---|---|
| 3,564,905 A | 2/1971 | Brenden et al. | 73/67.5 |
| 3,742,439 A | 6/1973 | Sheridon | 340/5 |
| 3,760,344 A | * 9/1973 | Hildebrand | 367/8 |
| 3,879,989 A | 4/1975 | Brenden | 73/67.5 |
| 3,911,729 A | 10/1975 | Collins | 73/67.5 H |
| 3,983,529 A | 9/1976 | Langlois | 340/5 |
| 4,028,934 A | 6/1977 | Sollish | 73/67.8 S |
| 4,478,481 A | 10/1984 | Fusek et al. | 350/3.83 |
| 4,531,410 A | 7/1985 | Crostack | 73/603 |
| 4,662,222 A | 5/1987 | Johnson | 73/602 |
| 5,179,455 A | 1/1993 | Garlick | 359/9 |
| 5,212,571 A | 5/1993 | Garlick et al. | 359/9 |
| 5,235,553 A | 8/1993 | Garlick et al. | 367/7 |
| 5,329,202 A | 7/1994 | Garlick et al. | 310/334 |
| 5,329,817 A | 7/1994 | Garlick et al. | 73/605 |
| 5,796,003 A | 8/1998 | Sandhu et al. | 73/603 |
| 5,999,836 A | 12/1999 | Nelson et al. | 600/407 |

OTHER PUBLICATIONS

Knoll, A. C., "Ultrasonic Holography Techniques for Localizing and Imaging Solid Objects", IEEE Transactions on RObotics an Automation, vol. 7, No. 4, Aug. 1991.*

* cited by examiner

*Primary Examiner*—Ian J. Lobo
(74) *Attorney, Agent, or Firm*—SEED IP Law Group PLLC

(57) ABSTRACT

There is disclosed a series of process and apparatus modifications to ultrasonic holography imaging systems that each or together function to enhance image quality of ultrasonic holography images. Specifically, there is disclosed a process and apparatus for generating multiple exposure ultrasonic holography images generated from selected orientations, each of which insures multiple images, multiple intensities (amplitudes) and multiple frequencies from each orientation. The inventive process and apparatus for providing multiple view, multiple angle, and multiple frequency or intensity transmissive ultrasound imaging of the internal structures of an object provides an object sound intensity of equal or near equal intensity across the entire field of the object, such as a human breast.

48 Claims, 10 Drawing Sheets

APPARATUS AND PROCESS MODIFICATIONS IN ULTRASONIC HOLOGRAPHY TO IMPROVE IMAGE QUALITY

TECHNICAL FIELD OF THE INVENTION

The present invention provides a series of process and apparatus modifications to ultrasonic holography imaging systems that each or together function to enhance image quality of ultrasonic holography images. Specifically, the present invention provides a process and apparatus for generating multiple exposure ultrasonic holography images generated from selected orientations, each of which insures multiple images, multiple intensities and multiple frequencies from each orientation. The inventive process and apparatus for providing multiple view, multiple angle, and multiple frequency or intensity transmissive ultrasound imaging of the internal structures of an object provides an object sound (ultrasound or ultrasonic energy) intensity of equal or near equal intensity across the entire field of the object, such as a human breast.

BACKGROUND OF THE INVENTION

A central element field of holography is fulfilled by combining or interfering an object wave or ultrasonic energy with a reference wave or ultrasonic energy to form an interference pattern referred to as the hologram. A fundamental requirement for the forming of the hologram and the practice of holography is that the initial source of the object wave and reference wave or energy are coherent with respect to the other wave. All parts of both the object wave and the reference wave are of the same frequency and of a defined orientation (a fixed spatial position and angle between the direction of propagation of the two sources). When performing holography the object wave is modified by interference with structure within the object of interest. As this object wave interacts with points of the object the three-dimensional features of the object impart identifying phase and amplitude changes on the object wave. Since the reference wave is an unperturbed (pure) coherent wave, its interference with the object wave results in an interference pattern which identifies the 3-D positioning and characteristics (ultrasonic absorption, diffraction, reflection, and refraction) of the scattering points of the object.

A second process, (the reconstruction of the hologram) is then performed when a coherent viewing source (usually light from a laser) is transmitted through or reflected from the hologram. The hologram pattern diffracts light from this coherent viewing or reconstructing source in a manner to represent the 3-D nature of the object, as seen by the ultrasonic object wave.

To reiterate, to perform holography coherent wave sources are required. This requirement currently limits practical applications of the practice of holography to the light domain (e.g., a laser light) or the domain of acoustics (sometimes referred to as ultrasound due to the practical application at ultrasonic frequencies) as these two sources are currently the only available coherent energy sources. Thus, further references to holography or imaging system will refer to the through transmission holographic imaging process that uses acoustical energies usually in the ultrasonic frequency range. In the practice of ultrasound holography, one key element is the source of the ultrasound, such as a large area coherent ultrasound transducer. A second key element is the projection of the object wave from a volume within the object (the ultrasonic lens projection system) and a third is the detector and reconstruction of the ultrasonic hologram into visual or useful format.

Although other configurations can be utilized, a common requirement of the source transducers for both the object and reference waves is to produce a large area plane wave having constant amplitude across the wave front and having a constant frequency for a sufficient number of cycles to establish coherence. Such transducers will produce this desired wave if the amplitude of the ultrasound output decreases in a Gaussian distribution profile as the edge of the large area transducer is approached. This decreasing of amplitude reduces or eliminates the "edge effect" from the transducer edge, which would otherwise cause varying amplitude across the wave front as a function distance from the transducer.

In the process of through transmission ultrasonic holographic imaging, an ultrasonic energy pulse from the object transducer progresses through the object, then through an acoustic focusing lens and at the appropriate time, the pulse of ultrasound is generated from the reference transducer such that the object wave and reference wave arrive at the detector at the same time to create a interference pattern (the hologram). For broad applications, the transducers need to be able to operate at a spectrum or bandwidth of discrete frequencies. Multiple frequencies allow comparisons and integration of holograms taken at selected frequencies to provide an improved image of the subtle changes within the object.

A hologram can also be formed by directing the object wave through the object at different angles to the central imaging axis of the lens means. This is provided by either positioning or rotating the object transducer around the central axis of the lens means or by using multiple transducers positioned such that the path of transmission of the sound is at an angle with respect to the central axis of the lens means.

With a through-transmission imaging system, it is important to determine the amount of resolution in the "z" dimension that is desirable and achievable. Since the holographic process operates without limits of mechanical or electronic devices but rather reconstructs images from wave interactions, the resolution achievable can approach the theoretical limit of one half the wavelength of the ultrasound used. However, it may be desirable to limit the "z" direction image volume so that one can "focus" in on one thin volume slice. Otherwise, the amount of information may be too great. Thus, it is of value to develop a means for projecting a planar slice within a volume into the detector plane. One such means is a large aperture ultrasonic lens means that will allow the imaging system to "focus" on a plane within the object. Additionally, this lens system and the corresponding motorized, computer controlled lens drive will allow one to adjust the focal plane and at any given plane to be able to magnify or demagnify at that z dimension position.

The image is detected and reconstructed at the detector. Standard photographic film may be used for the recording of light holograms and the 3-D image reconstructed by passing laser light through the film or reflecting it from the hologram pattern embossed on the surface of an optical reflective surface and reconstructing the image by reflecting light from the surface. However, there is no equivalent "film" material to record the intricate phase and amplitude pattern of a complex ultrasonic wave. One of the most common detectors uses a liquid-air surface or interface to record, in a dynamic way, the ultrasonic hologram formed. The sound energy at the frequency of ultrasound (above range of human hearing) will propagate with little attenuation through a liquid (such as water) but cannot propagate through air. At these higher frequencies (e.g., above 1 MHz) the ultrasound will not propagate through air because the wavelength of the sound energy is so short ($\lambda$(wavelength)=v/(velocity)/ f(frequency)). The density of air (approximately 0.00116 g/cm$^3$) is not sufficient to couple these short wavelengths and allow them to propagate. On the other hand the density of a liquid (e.g., water) is a favorable media to couple and propagate such sound. For example, the velocity of sound in air is approximately 330 meters/second whereas in water it is approximately 1497 meter/second. Thus, for water, both the density (1 g/cm$^3$) and the wavelength (~1.48 mm at 1 MHz) are significantly large such that ultrasound can propagate with little attenuation. Whereas, for air both the density (0.00116 g/cm$^3$) and wavelength (0.33 mm at 1 MHz) are sufficiently small such that the energy at these ultrasonic frequencies will not propagate.

Thus, when ultrasound propagating in a liquid encounters a liquid-air interface the entire amount of the energy is reflected back into the liquid. Since ultrasound (or sound) propagates as a mechanical force it is apparent that the reflection (or changing direction of propagation) will impart a forward force on this liquid air interface. This force, in turn, will distort the surface of the liquid. The amount of surface distortion will depend upon the amplitude of the ultrasound wave at each point being reflected and the surface tension of the liquid. Thus, the pattern of the deformation is the pattern of the phase and amplitude of the ultrasonic wave.

It is in this manner that a liquid-air interface can be commonly used to provide a near real-time recorder ("film equivalent") for an ultrasonic hologram. The shape of the surface deformation on this liquid-air detector is the representation of the phase and amplitude of the ultrasonic hologram formed by the interference of the object and reference ultrasonic waves.

The greatest value of the ultrasonic holographic process is achieved by reconstructing the hologram in a usable manner, usually in light, to make visible the structural nature of the initial object. In the case of a liquid-air interface, the reconstruction to achieve the visible image is accomplished by reflecting a coherent light from this liquid-air surface. This is the equivalent process to reflecting laser light from optically generated hologram that is embossed on the surface of a reflecting material (e.g., thin aluminum film).

The reflected light is diffracted (scattered) by the hologram to diffracted orders, each of which contains image information about the object. These diffracted orders are referred to as ±n th orders. That part of the reconstructing light that does not interact with the hologram is referred to as zero order and is usually blocked so that the weaker diffracted orders can be imaged. The higher the diffracted order the greater the separation angle from the zero order of reflected light.

Once reconstructed, the image may be viewed directly, by means of a video camera or through post processing.

Ultrasonic holography as typically practiced is illustrated in FIG. 1. A plane wave of sound (1a) (ultrasound) is generated by the large area transducer (1) for passing through an object 15 (U.S. Pat. No. 5,329,202). The sound is scattered (diffracted) by structural points within the object 15 to the focal plane (2). The object may be held in place by on object holder 17. This sound (2a) is scattered from the internal object points that lie in the focal plane (2) are focused (projected) into the ultrasonic hologram plane (6). The focusing takes place by use of ultrasonic lens (3) (U.S. Pat. No. 5,235,553) which focuses the scattered sound into a hologram detector surface (6) and the unscattered sound into a focal point (4). The lens means also allows the imaging process to magnify the image or change focus position (U.S. Pat. No. 5,212,571). Since the focus point of the unscattered sound (4) is prior to the holographic detector plane (6), this portion of the total sound again expands to form the transparent image contribution (that portion of the sound that transmitted through the object as if it were transparent or semitransparent). In such an application, an ultrasound reflector (5) is generally used to direct the object sound at a different angle (preferably vertically to allow for the holographic detector to have a surface parallel to ground to avoid gravity effects), thus impinging on horizontal detector plane usually containing a liquid which is deformed by the ultrasound reflecting from the liquid-air interface. When the reference wave (7) and the object wave are simultaneous reflected from this detector, the deformation of the liquid-air interface is the exact pattern of the ultrasonic hologram formed by the object wave (1a combined with 2a) and the "off-axis" reference wave (7).

This ultrasonic hologram formed in the holographic detector (6) is subsequently, reconstructed for viewing by using a coherent light source (9), which may be passed through an optical lens (8), and reflected from the holographic detector surface (U.S. Pat. No. 5,179,455). This reflected coherent light contains two components. These are A: The light that is reflected from the ultrasound hologram which was not diffracted by the ultrasonic holographic pattern which is focused at position (10) and referred to as undiffracted or zero order light; and B: The light that does get diffracted from/by the ultrasonic hologram is reflected at an "off-axis" angle from the zero order at position (11) and referred to as the "first order" image view when passed through a spatial filter (12). It is noted that this reconstruction method produces multiple diffraction orders each containing the ultrasonic object information. Note also both + and − multiple orders of the diffracted image are present and can be used individually or in combinations to view the optical reconstructed image from the ultrasonically formed hologram by modifying the spatial filter (12) accordingly.

Commercial application of ultrasonic holography has been actively pursued over many years, yet only limited results have been achieved. The application of ultrasonic holography may have its greatest commercial utility for non-destructive testing of materials and imaging of internal structures in soft tissue. One of the problems often encountered is consistency and quality of images obtained. It is difficult to obtain undistorted images of selected internal structures within objects (such as a human breast) due to interference or shadowing of other out-of-focus structures within the object.

Therefore, there is a need in the art to improve image quality by recognizing and utilizing the effects of diffraction generated by internal structures within the object. This need is particularly strong for breast cancer screening techniques that now utilize invasive mammography (providing the patient with a dose of radiation from XRay imaging) and yet do not produce images that are sensitive to detecting some lesions and do not lend a sense of three dimensional structure to breast tissue.

That portion of the ultrasound wave that passes through the imaged object without being scattered by structures within the object can be a major contributor in "semitransparent objects" (that is, an object that scatters a small portion of the sound waves directed at the object). Since many objects of interest can be rather transparent to sound, (e.g. human soft tissue normal structures and tumor tissue of solid tumors) there is formed a bright and strong white light contribution to the image from this sound that does not interfere with the object. When one wants to detect and determine the characteristic of subtle changes in the object (e.g., determining tissue characteristics) this background bright image contribution can overpower the resolution of small and subtle contributions of tissue change. Therefore, there is a need in the art to improve resolution characteristics of transmissive ultrasonic imaging so as to be able to distinguish subtle differences within the object (i.e., so as to be able to image tumor tissue within surrounding soft breast tissue).

In U.S. Pat. No. 5,329,817, an ultrasonic holography imaging process and apparatus embodiment is disclosed that provides for a rotating single ultrasonic transducer 50, 54 and 76 as shown in FIGS. 2A, 2B and 2C respectively which correspond to FIGS. 7, 8 and 9, respectively from U.S. Pat. No. 5,329,517 an angled rectangular transducer at an angle θ with respect to the normal plane or axis 51 of the "system" (e.g., centerline of the acoustic lens means) is used. The single ultrasonic transducer element 50 (or 54 or 76) is angled (θ) at an acute incidence angle relative to the optical axis to better remove imaging shadows from out-of-focus (i.e., the focal plane of the object) internal structures of the object.

SUMMARY OF THE INVENTION

The present invention provides a series of incremental improvements to the process of ultrasonic holography imaging, especially in imaging for tumor masses in soft tissue, and to a series of incremental apparatus improvements to an ultrasonic holographic imaging device. Each incremental improvement to either the apparatus or process or both, provided herein is able to incrementally improve holographic image quality. Therefore, the claimed invention is directed to each incremental improvement alone or to any combination of incremental improvements (in a matrix) reflected in the ultrasonic holographic imaging process and apparatus.

The present invention provides an ultrasonic holography imaging apparatus comprising:

(a) a plurality of ultrasonic transducers directing ultrasonic energy in the form of a wave toward an object to be imaged, wherein the plurality of ultrasonic transducers are oriented around a central axis of rotation on a rotating device;

(b) an acoustic lens means for focusing the ultrasonic energy to a focal point downstream of a first lens and having a centerline, wherein the lens means comprises one or a plurality of lenses, wherein the focal point is location at which the wave energy is focused; and (c) a holographic detector having a surface aligned perpendicular to the centerline of the acoustic lens means.

Preferably, the wave generated by each transducer is a planar, spherical or cylindrical wave directed at a plane perpendicular to the direction of transmission. Preferably, the apparatus further comprises an acoustically opaque element selectively positioned at the focal point of the lens (i.e., the point of focus of a wave of energy generated at infinity) to selectively only pass or only prevent transmission of ultrasonic energy directed to the focal point. Most preferably, the acoustically opaque element is made from an acoustical insulating material having entrapped voids or air.

Most preferably, the acoustical insulating material is selected from the group consisting of cork, porous polymers, open or closed cell foams, and combinations thereof. Preferably, the acoustic lens means focuses the planar, spherical, or cylindrical wave to a focal point and any generated diffraction waves generated within the object at the hologram detector surface. Preferably, the apparatus further comprises a reflective means to direct the ultrasonic energy in the form of a wave that passes through the object being imaged to a vertical orientation.

The present invention further provides a process for improving image quality (better imaging of subtle structures) in an ultrasonic imaging apparatus, wherein the ultrasonic imaging apparatus comprises a transducer assembly, an object holder surrounded by acoustically transmissive media, an acoustic lens assembly, and a holographic image detection system, and wherein the transducer assembly electric control means for controlling frequency, power, timing and duration of ultrasonic output pulse of the transducer(s) and a one or a plurality of a transducers, wherein the transducer(s) are mounted on a movable support having a center axis, comprising the steps of:

(a) providing an object to be internally imaged to be held by the object holder;

(b) transmitting a pulse sequence of ultrasound, each pulse within the sequence comprises a plurality of cycles of a single frequency ($f$) of ultrasound, wherein each sequence comprises multiple frequency pulses ($f_1, f_2, f_3, \ldots f_n$); and (c) imaging the object from a hologram formed in the holographic detection system for each pulse within the sequence.

Preferably, the process further comprises either capturing each separate image for separate analysis for a specific frequency, or averaging a plurality of images from selected frequencies to form a composite image derived from the selected frequencies. Most preferably, the imaging technique utilizes an apparatus having an acoustically opaque element selectively positioned at the focal point of the sound energy that is not scattered by the object to prevent only (dark background image) or to pass only (white background image) transmission of ultrasonic energy directed to the focal point. Most preferably, the acoustically opaque element is made from an acoustical insulating material having entrapped voids or air. Most preferably, the acoustical insulating material is selected from the group consisting of cork, porous polymers, open or closed cell foams, and combinations thereof Preferably, the transmitting the pulse sequence of multiple frequencies chooses the frequencies to have equal incremental increases of each frequency. Most preferably, the process further comprises either capturing each separate image for separate analysis for a specific frequency, or averaging a plurality of images from selected frequencies to form a composite image derived from the selected frequencies. Preferably, the transducer(s) transmit each pulse sequence of ultrasound having a plurality of cycles of a single frequency or having multiple frequencies at a single acute incidence angle (θ) or at multiple acute incidence angles ($\theta_1, \theta_2, \theta_3, \ldots \theta_n$). Most preferably, the process further comprises either capturing each separate image for separate analysis for a specific frequency, or averaging a plurality of images from selected frequencies to form a composite image derived from the selected frequencies.

Preferably, the transducer(s) transmit each pulse sequence of ultrasound having a plurality of cycles of a single frequency or at multiple frequencies at a single amplitude (power, A) or at multiple amplitudes ($A_1, A_2, A_3, \ldots A_n$). Most preferably, the process further comprises either capturing each separate image for separate analysis for a specific frequency, or averaging a plurality of images from selected frequencies to form a composite image derived from the selected frequencies.

The present invention further provides an ultrasonic imaging apparatus for improving ultrasonic holography image quality (better imaging of subtle structures comprising a transducer assembly, an object holder surrounded by acoustically transmissive media, an acoustic lens assembly, and a holographic image detection system, wherein the transducer assembly electric control means for controlling frequency, power, timing and duration of ultrasonic output pulse of the transducer(s) and a one or a plurality of a transducers, wherein the transducer(s) are mounted on a movable support having a center axis, and wherein the transducer assembly transmits a pulse sequence of ultrasound, wherein each pulse within the sequence comprises a plurality of cycles of a single frequency ($f$) of ultrasound, wherein each sequence comprises multiple frequency pulses ($f_1, f_2, f_3, \ldots f_n$). Preferably, the apparatus further comprises an image analysis assembly that either captures each separate image for separate analysis for a specific frequency, or averages a plurality of images from selected frequencies to form a composite image derived from the selected frequencies. Most preferably, the imaging technique utilizes an apparatus having an acoustically opaque element selectively positioned at the focal point to prevent only (dark background image) or pass only transmission of ultrasonic energy directed to the focal point (white background image). Most preferably, the acoustically opaque element is made from an acoustical insulating material having entrapped voids or air. Most preferably, the acoustical insulating material is selected from the group consisting of cork, porous polymers, open or closed cell foams, and combinations thereof. Preferably, the transducer assembly transmits the pulse sequence of multiple frequencies and chooses the frequencies to have equal incremental increases of each frequency. Most preferably, the apparatus further comprises an image analysis assembly that either captures each separate image for separate analysis for a specific frequency, or averages a plurality of images from selected frequencies to form a composite image derived from the selected frequencies. Preferably, the transducer(s) transmit each pulse sequence of ultrasound having a plurality of cycles of a single frequency or at multiple frequencies at a single acute incidence angle ($\theta$) or at multiple acute incidence angles ($\theta_1, \theta_2, _3, \ldots \theta_n$). Most preferably, the apparatus further comprises and image analysis assembly that either captures each separate image for separate analysis for a specific frequency, or averages a plurality of images from selected frequencies to form a composite image derived from the selected frequencies.

Preferably, the transducer(s) transmit each pulse sequence of ultrasound having a plurality of cycles of a single frequency or at multiple frequencies at a single amplitude (power, A) or at multiple amplitudes ($A_1, A_2, A_3, \ldots A_n$). Most preferably, the apparatus further comprises an image analysis assembly that either captures each separate image for separate analysis for a specific frequency, or averages a plurality of images from selected frequencies to form a composite image derived from the selected frequencies.

The present invention further provides a process for improving image quality (better imaging of subtle structures) in an ultrasonic imaging apparatus, wherein the ultrasonic imaging apparatus comprises a transducer assembly, an object holder surrounded by acoustically transmissive media, an acoustic lens assembly, and a holographic image detection system, and wherein the transducer assembly electric control means for controlling frequency, power, timing and duration of ultrasonic output pulse of the transducer(s) and a one or a plurality of a transducers, wherein the transducer(s) are mounted on a movable support having a center axis, comprising the steps of:

(a) providing an object to be internally imaged while being held by the object holder;

(b) transmitting a pulse sequence of ultrasound, each pulse within the sequence comprises a plurality of cycles of a single frequency ($f$) of ultrasound, wherein each sequence comprises a variable angle of incidence ($\theta$) of transmission from a plurality of transducer elements in the transducer assembly; and (c) imaging the object from a hologram formed in the holographic detection system for each pulse within the sequence.

Preferably, the process further comprises either capturing each separate image for separate analysis for a specific frequency, or averaging a plurality of images from selected frequencies to form a composite image derived from the selected frequencies. Most preferably, the imaging technique utilizes an apparatus having an acoustically opaque element selectively positioned at the focal point to prevent only (dark background image) or pass only transmission of ultrasonic energy directed to the focal point (white background image). Most preferably, the acoustically opaque element is made from an acoustical insulating material having entrapped voids or air. Most preferably, the acoustical insulating material is selected from the group consisting of cork, porous polymers, open or closed cell foams, and combinations thereof. Preferably, the transmitting the pulse sequence of multiple frequencies chooses the frequencies to have equal incremental increases of each frequency. Most preferably, the process further comprises either capturing each separate image for separate analysis for a specific frequency, or averaging a plurality of images from selected frequencies to form a composite image derived from the selected frequencies. Preferably, the transducer(s) transmit each pulse sequence of ultrasound having a plurality of cycles at multiple frequencies. Most preferably, the process further comprises either capturing each separate image for separate analysis for a specific frequency, or averaging a plurality of images from selected frequencies to form a composite image derived from the selected frequencies.

Preferably, the transducer(s) transmit each pulse sequence of ultrasound having a plurality of cycles of a single frequency or at multiple frequencies at a single amplitude (power, A) or at multiple amplitudes ($A_1, A_2, A_3, \ldots A_n$). Most preferably, the process further comprises either capturing each separate image for separate analysis for a specific frequency, or averaging a plurality of images from selected frequencies to form a composite image derived from the selected frequencies.

The present invention further provides an ultrasonic imaging apparatus for improving ultrasonic holography image quality (better imaging of subtle structures comprising a transducer assembly, an object holder surrounded by acoustically transmissive media, an acoustic lens assembly, and a holographic image detection system, wherein the transducer assembly electric control means for controlling frequency, power, timing and duration of ultrasonic output pulse of the transducer(s) and a plurality of a transducer elements for transmission of ultrasound, wherein the transducer elements are mounted on a movable support having a center axis movable at an angle of incidence ($\theta$), and wherein the transducer assembly transmits a pulse sequence of ultrasound, wherein each pulse within the sequence comprises a plurality of cycles of a single frequency ($f$) of ultrasound, wherein each sequence comprises a single or multiple frequency pulses ($f_1, f_2, f_3, \ldots f_n$). Preferably, the apparatus further comprises an image analysis assembly that either captures each separate image for separate analysis for a specific frequency, or averages a plurality of images from selected frequencies to form a composite image derived from the selected frequencies. Most preferably, the imaging technique utilizes an apparatus having an acoustically opaque element selectively positioned at the focal point to prevent only (dark background image) transmission of ultrasonic energy directed to the focal point (white background image). Most preferably, the acoustically opaque element is made from an acoustical insulating material having entrapped voids or air. Most preferably, the acoustical insulating material is selected from the group consisting of cork, porous polymers, open or closed cell foams, and combinations thereof. Preferably, the transducer assembly transmits the pulse sequence of multiple frequencies and chooses the frequencies to have equal incremental increases of each frequency. Most preferably, the apparatus further comprises an image analysis assembly that either captures each separate image for separate analysis for a specific frequency, or averages a plurality of images from selected frequencies to form a composite image derived from the selected frequencies. Preferably, the transducer(s) transmit each pulse sequence of ultrasound having a plurality of cycles of a single frequency or at multiple frequencies at a single amplitude (power, A) or at multiple amplitudes ($A_1, A_2, A_3, \ldots A_n$). Most preferably, the apparatus further comprises and image analysis assembly that either captures each separate image for separate analysis for a specific frequency, or averages a plurality of images from selected frequencies to form a composite image derived from the selected frequencies.

The present invention further provides a process for improving image quality (better imaging of subtle structures) in an ultrasonic imaging apparatus, wherein the ultrasonic imaging apparatus comprises a transducer assembly, an object holder surrounded by acoustically transmissive media, an acoustic lens assembly, and a holographic image detection system, and wherein the transducer assembly electric control means for controlling frequency, power, timing and duration of ultrasonic output pulse of the transducer(s) and a one or a plurality of a transducers, wherein the transducer(s) are mounted on a movable support having a center axis, comprising the steps of:

(a) providing an object to be internally imaged to be held by the object holder;

(b) transmitting a pulse sequence of ultrasound, each pulse within the sequence comprises a plurality of cycles of a single frequency ($f$) of ultrasound, wherein each sequence comprises a variable amplitude of the pulse (A) of transmission; and (c) imaging the object from a hologram formed in the holographic detection system for each pulse within the sequence.

Preferably, the process further comprises either capturing each separate image for separate analysis for a specific frequency, or averages a plurality of images from selected frequencies to form a composite image derived from the selected frequencies. Most preferably, the imaging technique utilizes an apparatus having an acoustically opaque element selectively positioned at the focal point to prevent only (dark background image) or pass only transmission of ultrasonic energy directed to the focal point (white background image). Most preferably, the acoustically opaque element is made from an acoustical insulating material having entrapped voids or air. Most preferably, the acoustical insulating material is selected from the group consisting of cork, porous polymers, open or closed cell foams, and combinations thereof. Preferably, the transmitting the pulse sequence of multiple frequencies chooses the frequencies to have equal incremental increases of each frequency. Most preferably, the process further comprises either capturing each separate image for separate analysis for a specific frequency, or averaging a plurality of images from selected frequencies to form a composite image derived from the selected frequencies. Preferably, the transducer(s) transmit each pulse sequence of ultrasound having a plurality of cycles at multiple frequencies. Most preferably, the process further comprises either capturing each separate image for separate analysis for a specific frequency, or averaging a plurality of images from selected frequencies to form a composite image derived from the selected frequencies. Preferably, the transducer(s) transmit each pulse sequence of ultrasound having a plurality of cycles of a single frequency or at multiple frequencies at a single acute incidence angle ($\theta$) or at multiple acute incidence angles ($\theta_1, \theta_2, \theta_3, \ldots \theta_n$). Most preferably, the apparatus further comprises and image analysis assembly that either captures each separate image for separate analysis for a specific frequency, or averages a plurality of images from selected frequencies to form a composite image derived from the selected frequencies.

The present invention further provides an ultrasonic imaging apparatus for improving ultrasonic holography image quality (better imaging of subtle structures) comprising a transducer assembly, an object holder surrounded by acoustically transmissive media, an acoustic lens assembly, and a holographic image detection system, wherein the transducer assembly electric control means for controlling frequency, power, timing and duration of ultrasonic output pulse of the transducer(s) and a plurality of a transducer elements for transmission of ultrasound, wherein the transducer elements are mounted on a movable support having a center axis movable at an angle of incidence ($\theta$), and wherein the transducer assembly transmits a pulse sequence of ultrasound, wherein each pulse within the sequence comprises a plurality of cycles of a single frequency ($f$) of ultrasound, wherein each sequence comprises a single or multiple frequency pulses ($f_1, f_2, f_3, \ldots f_n$) and multiple amplitudes ($A_1, A_2, A_3, \ldots A_n$). Preferably, the apparatus further comprises an image analysis assembly that either captures each separate image for separate analysis for a specific frequency, or averages a plurality of images from selected frequencies to form a composite image derived from the selected frequencies. Most preferably, the imaging technique utilizes an apparatus having an acoustically opaque element selectively positioned at the focal point to prevent only (dark background image) or pass only transmission of ultrasonic energy directed to the focal point (white background image). Most preferably, the acoustically opaque element is made from an acoustical insulating material having entrapped voids or air. Most preferably, the acoustical insulating material is selected from the group consisting of cork, porous polymers, open or closed cell foams, and combinations thereof. Preferably, the transducer assembly transmits the pulse sequence of multiple frequencies and chooses the frequencies to have equal incremental increases of each frequency. Most preferably, the apparatus further comprises and image analysis assembly that either captures each separate image for separate analysis for a specific frequency, or averages a plurality of images from selected frequencies to form a composite image derived from the selected frequencies. Preferably, the transducer(s) transmit each pulse sequence of ultrasound having a plurality of cycles of a single frequency or at multiple frequencies at a single amplitude (power, A) or at multiple amplitudes ($A_1, A_2, A_3, \ldots A_n$). Most preferably, the apparatus further comprises and image analysis assembly that either captures each separate image for separate analysis for a specific frequency, or averages a plurality of images from selected frequencies to form a composite image derived from the selected frequencies.

DETAILED DESCRIPTION OF THE INVENTION

Figure 1:
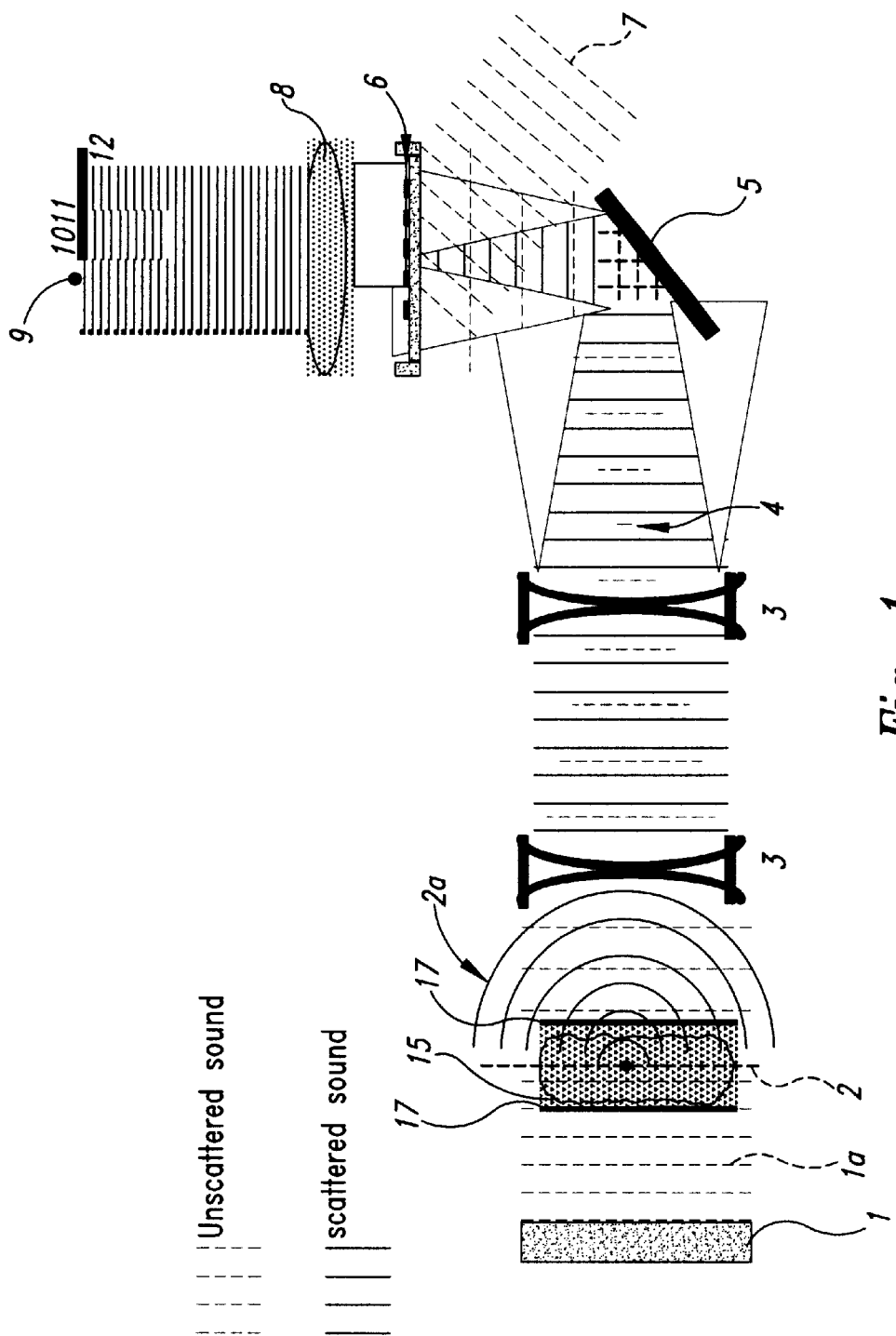
FIG. 1 shows the state of the prior art illustrating the operation of ultrasonic holography (Garlick et al. U.S. Pat. No. 5,329,817). Specifically, a plane wave of sound (1a) (ultrasound or ultrasonic energy) is generated by a large area transducer (1) for passing through an object 15 (U.S. Pat. No. 5,329,202). The sound is scattered (diffracted) by structural points within the object 15 at the focal plane (2). The object may be held in place by on object holder 17. This sound scattered (2a) from the internal object points that lie in the focal plane are focused (projected) into the ultrasonic hologram plane (6). The focusing takes place by use of an ultrasonic lens (3) (U.S. Pat. No. 5,235,553) which focuses the scattered sound into a hologram detector surface (6) and the unscattered sound into a point (4). Since the focal point of the unscattered sound (4) is prior to the holographic detector plane (6), this portion of the total sound again expands to form the transparent image contribution (that portion of the sound that transmitted through the object as if it were transparent or semitransparent). In such an application, an ultrasound reflector means (5) is used to direct the scattered and unscattered ultrasonic energy at a different angle (preferably vertically to allow for the holographic detector to have a surface parallel to ground to avoid gravity effects), thus impinging on horizontal detector plane usually containing a liquid which is deformed by the ultrasound reflecting from the liquid-air interface. When the reference wave (7) and the object wave are simultaneous reflected from this detector, the deformation of the liquid-air interface is the exact pattern of the ultrasonic hologram formed by the object wave and the "off-axis" reverence wave (7). If no object is present, the image produced by the apparatus of FIG. 1 is a completely white image. If there is a completely acoustically opaque element, the image will be black.
Figure 2A:
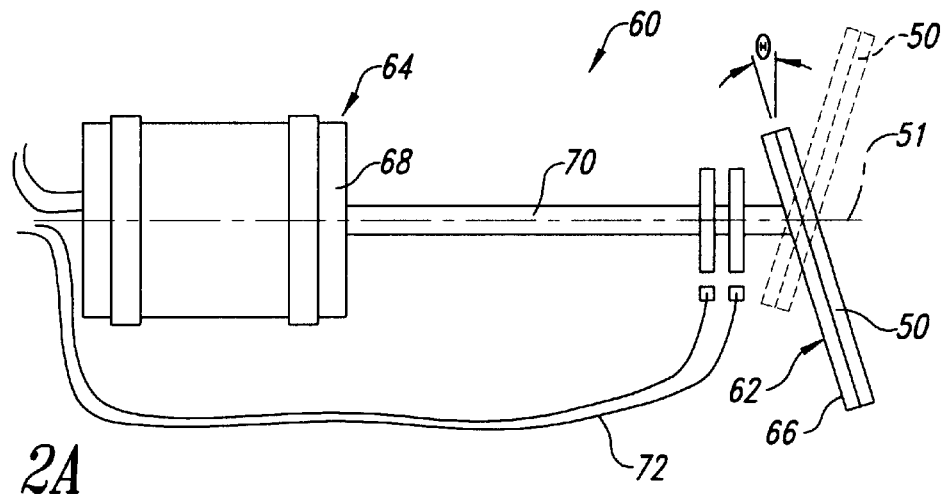
FIGS. 2A, 2B and 2C show a rotating angled transducer previously described in U.S. Pat. No. 5,329,817, the disclosure of which is incorporated by reference herein. This rotating transducer provides sound waves which are generated at various radial angles around the axis of rotation and at all times having a direction of propagation that forms an angle with the axis of rotation. The purpose of this arrangement is to view structures from different angles such that contributions from structures out of the focal plane are minimized.
Figure 2B:
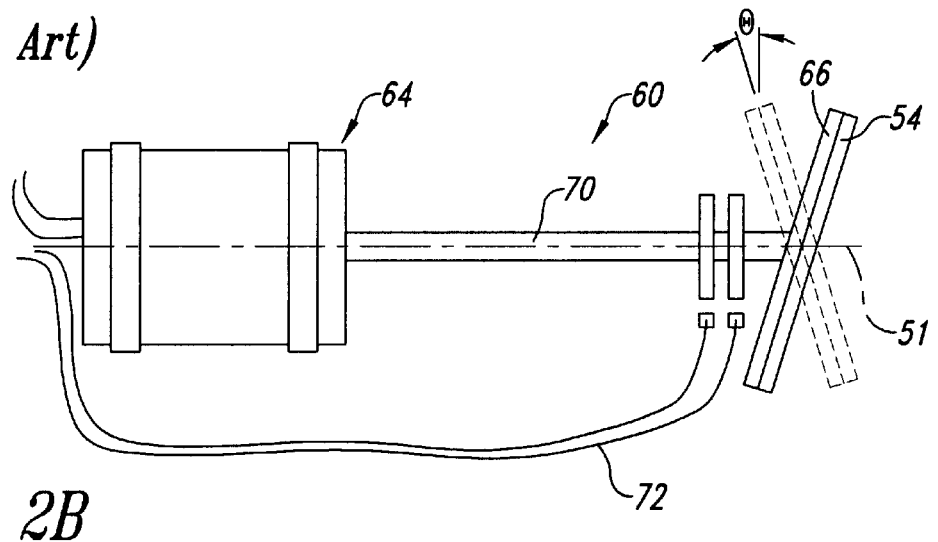
Figure 2C:
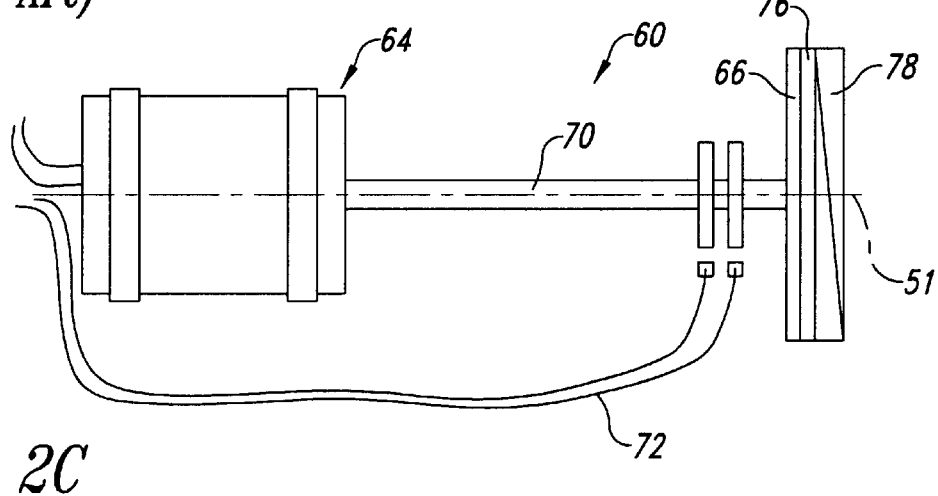
Figure 3A:
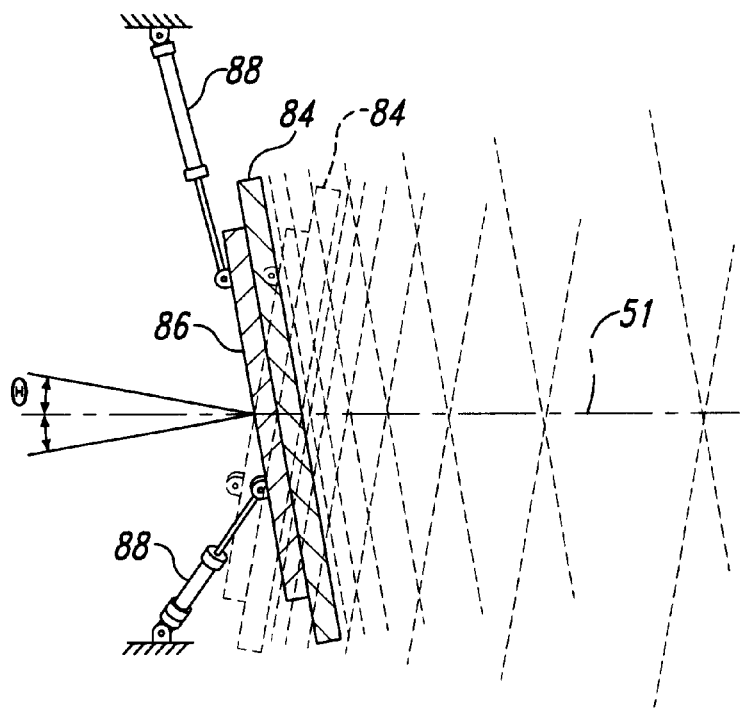
FIGS. 3A and 3B show an oscillating transducer previously described in U.S. Pat. No. 5,329,817. This oscillating transducer provides sound waves (i.e., ultrasonic energy) that are propagated at varying angles with respect to the central axis of oscillation that, preferably, is the center axis of the lens means.
Figure 3B:
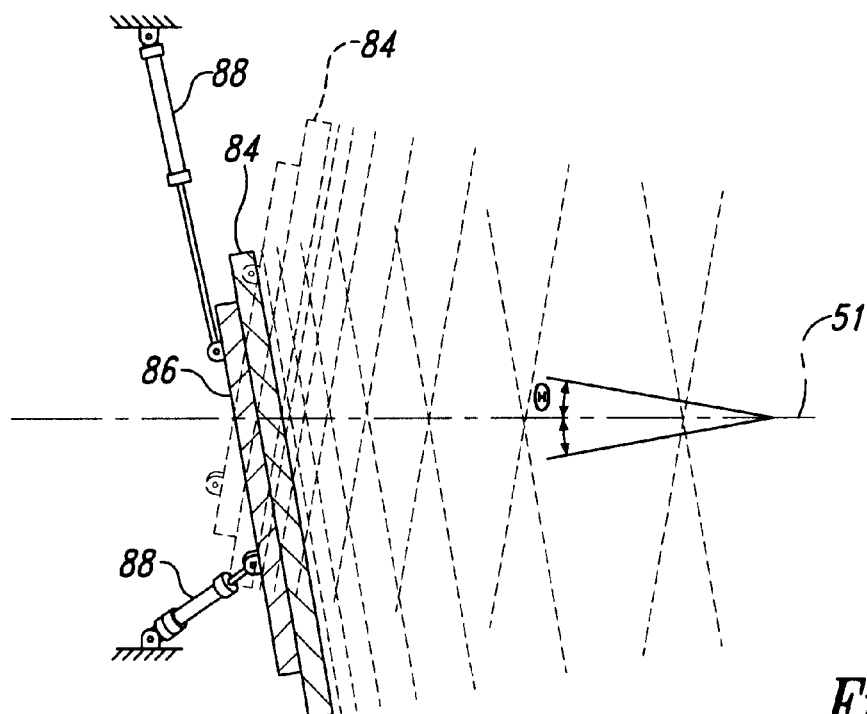
Figure 4:
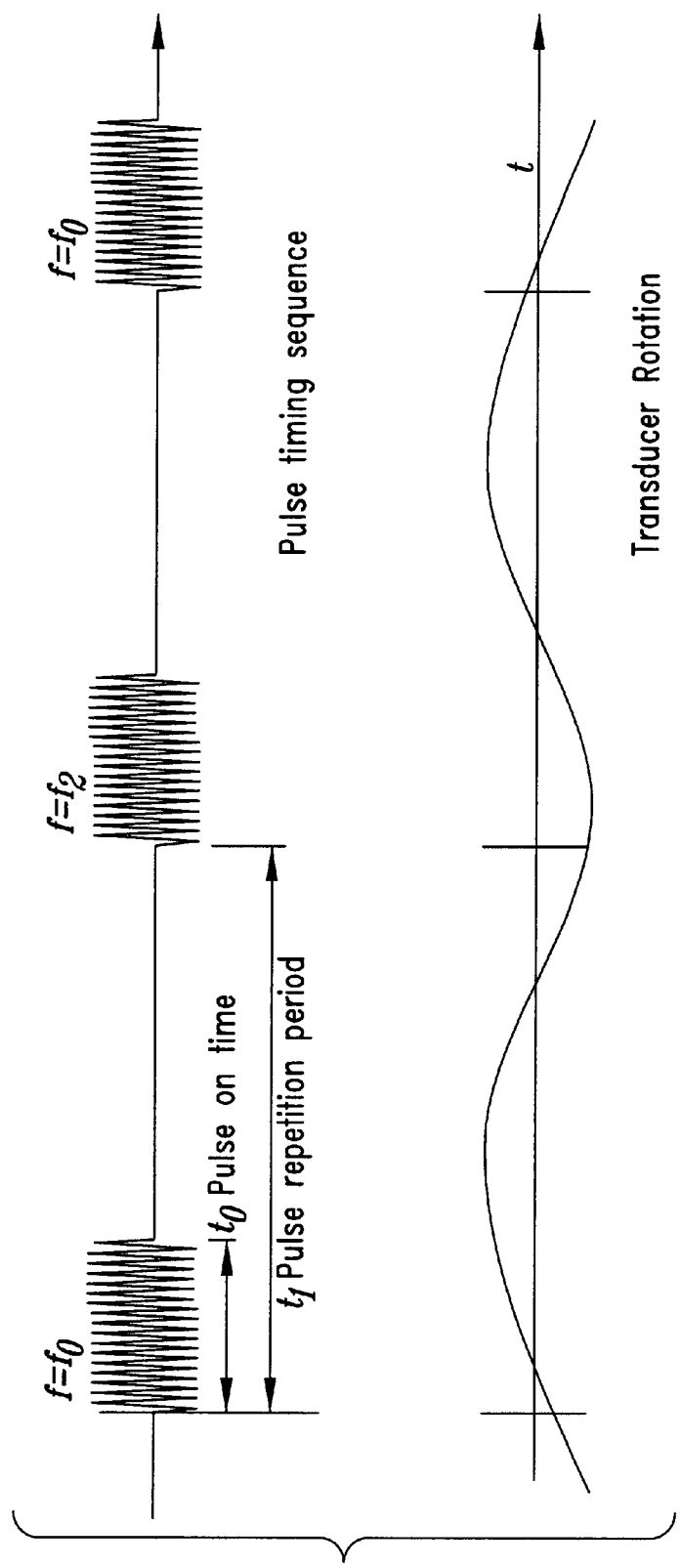
FIG. 4 shows an illustration of the image time sequence of sound pulses according to one embodiment of the present invention. It should be noted that that the position of image in the rotation is random. In other words the rotation or oscillation of the transducer is not synched to the timing of the pulse sequence.
Figure 5:
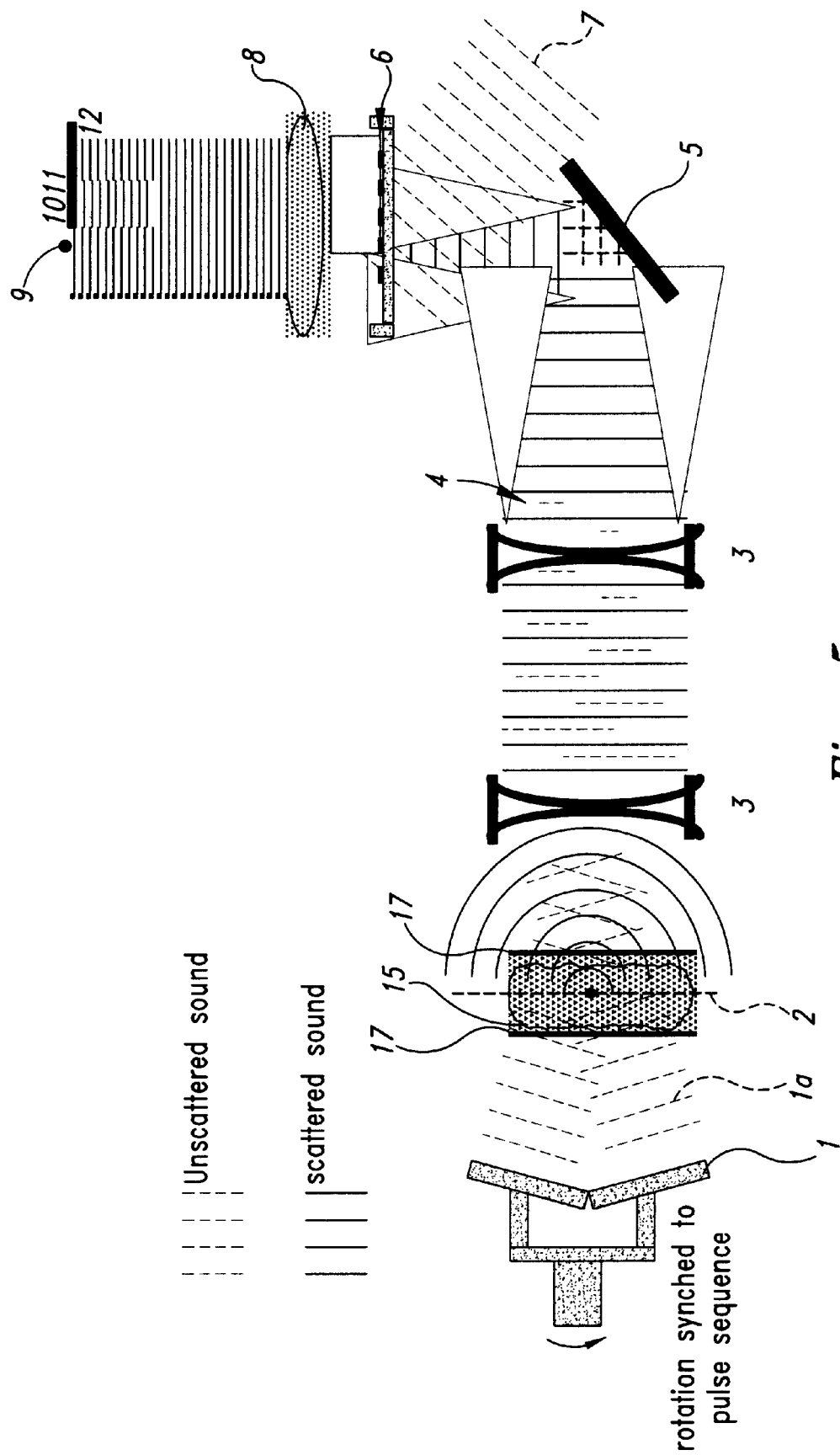
FIG. 5 shows a transducer assembly of the present invention showing multiple (in this illustration two) transducer elements. The illustrated transducer assembly contains two transducer elements angled with respect to a rotation axis.
Figure 6:
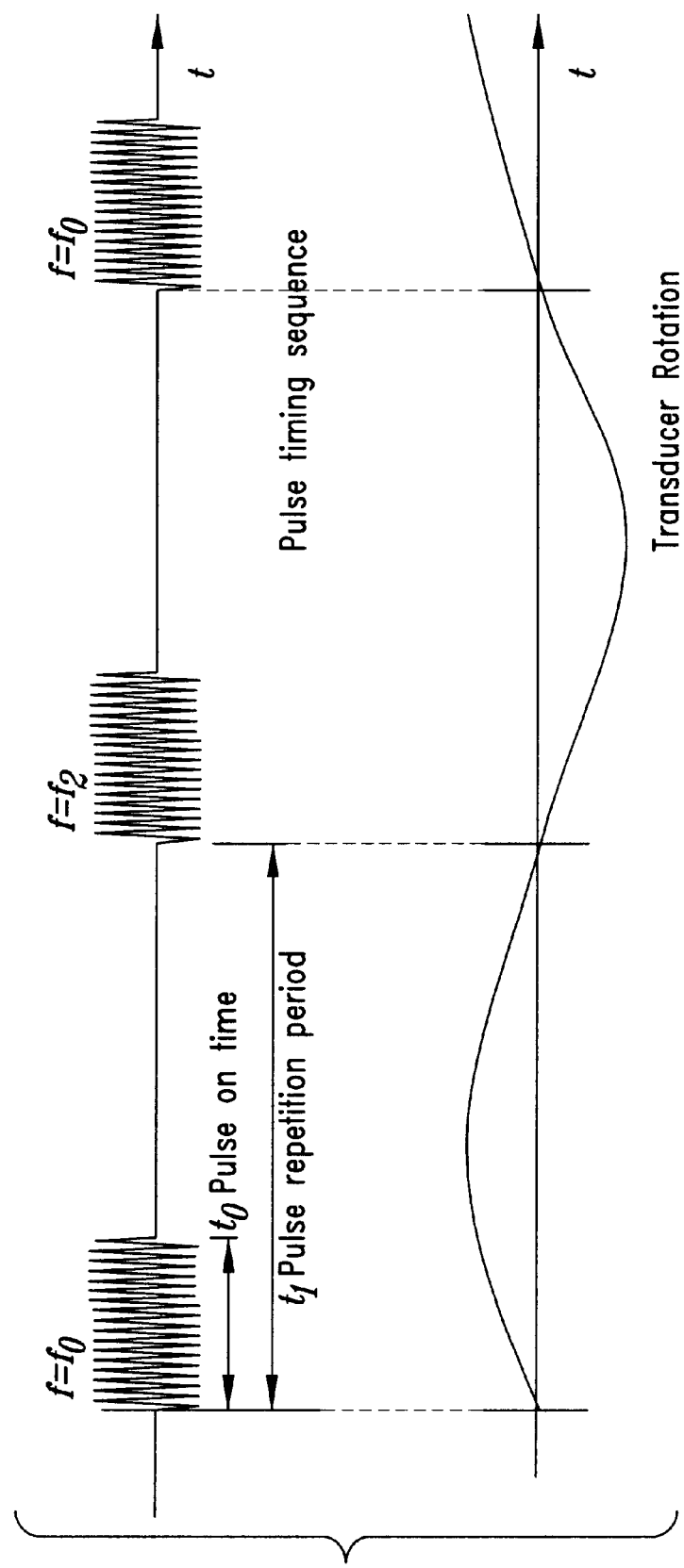
FIG. 6 shows a pulse time sequence that synchronizes the pulse timing to the rotation of oscillation of the transducer means. In this embodiment, the pulse timing is repeated at a given rotation or oscillation position, as illustrated. In this embodiment, the structure of interest is viewed for a given sequence at a repeated angular view. The image is synchronized with rotation or oscillation to maintain a consistent transducer element position and allow for variation of only frequency, and amplitude.
Figure 7:
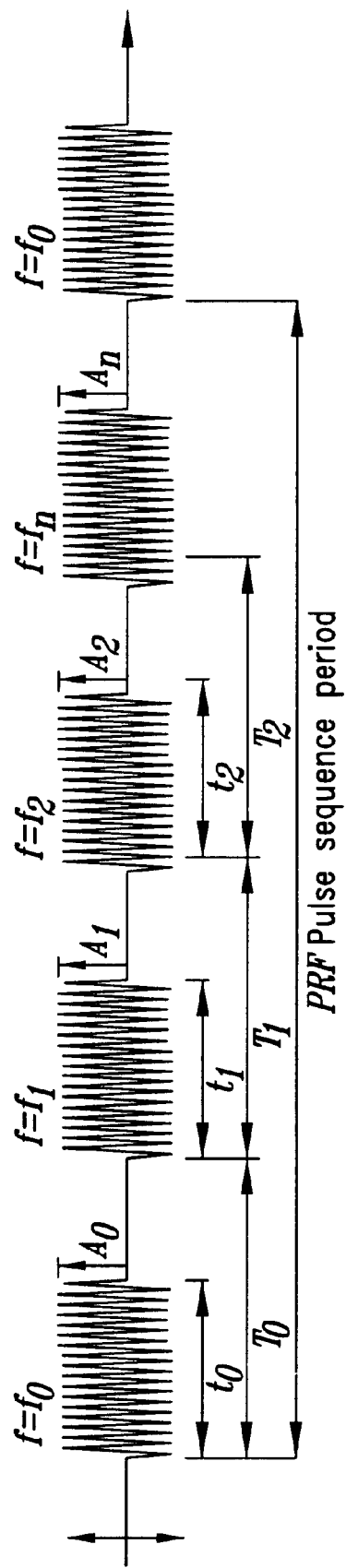
FIG. 7 shows a time line illustration of a pulsed single frequency fixed amplitude system. F is the frequency of ultrasound transmission from the transducer within a pulse $f_0 = f_1 = f_{n-1} = f_n$. t is the "on time" of the pulse $t_0 = t_1 = t_{n-1} = t_n$. T is the "period" or the time between the start of each pulse and the start of the next pulse $T_0 = T_1 = T_{n-1} = T_n$. R is the repetition (rep) rate of the pulses wherein R=1/T.
Figure 8:
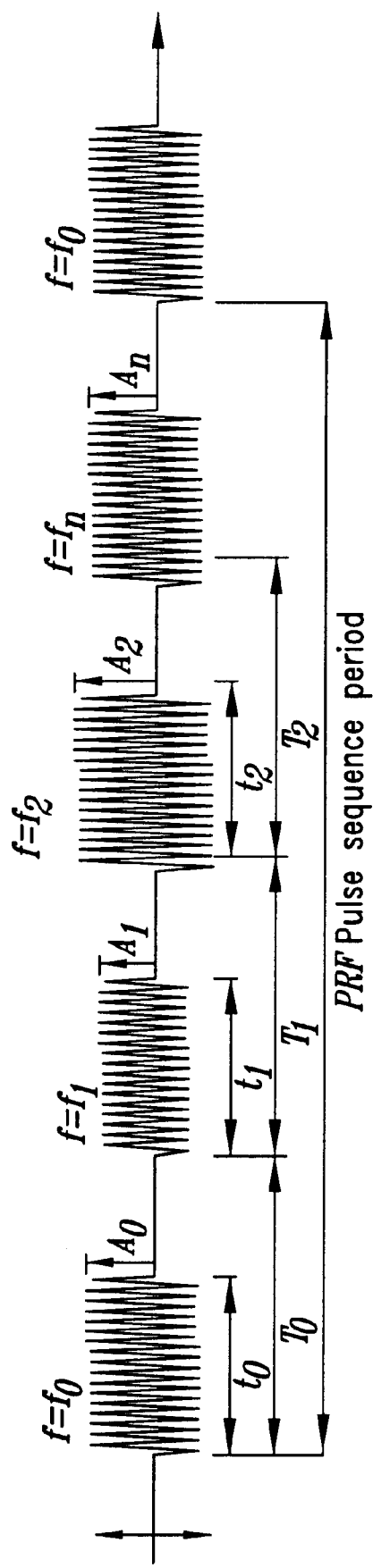
FIG. 8 shows a time line illustration of a pulsed single frequency but having variable amplitude system. F is the frequency of ultrasound transmission (from the transducer) within a, pulse $f_0 = f_1 = f_{n-1} = f_n$. t is the "on time" of the pulse $t_0 = t_1 = t_{n-1} = t_n$. T is the "period" or the time between the start of each pulse and the start of the next pulse $T_0 = T_1 = T_{n-1} = T_n$. R is the repetition (rep) rate of the pulses wherein R=1/T. The frequency pulses do not have equal amplitudes such that higher amplitudes may be selected from higher frequencies to account for signal attenuation.
Figure 9:
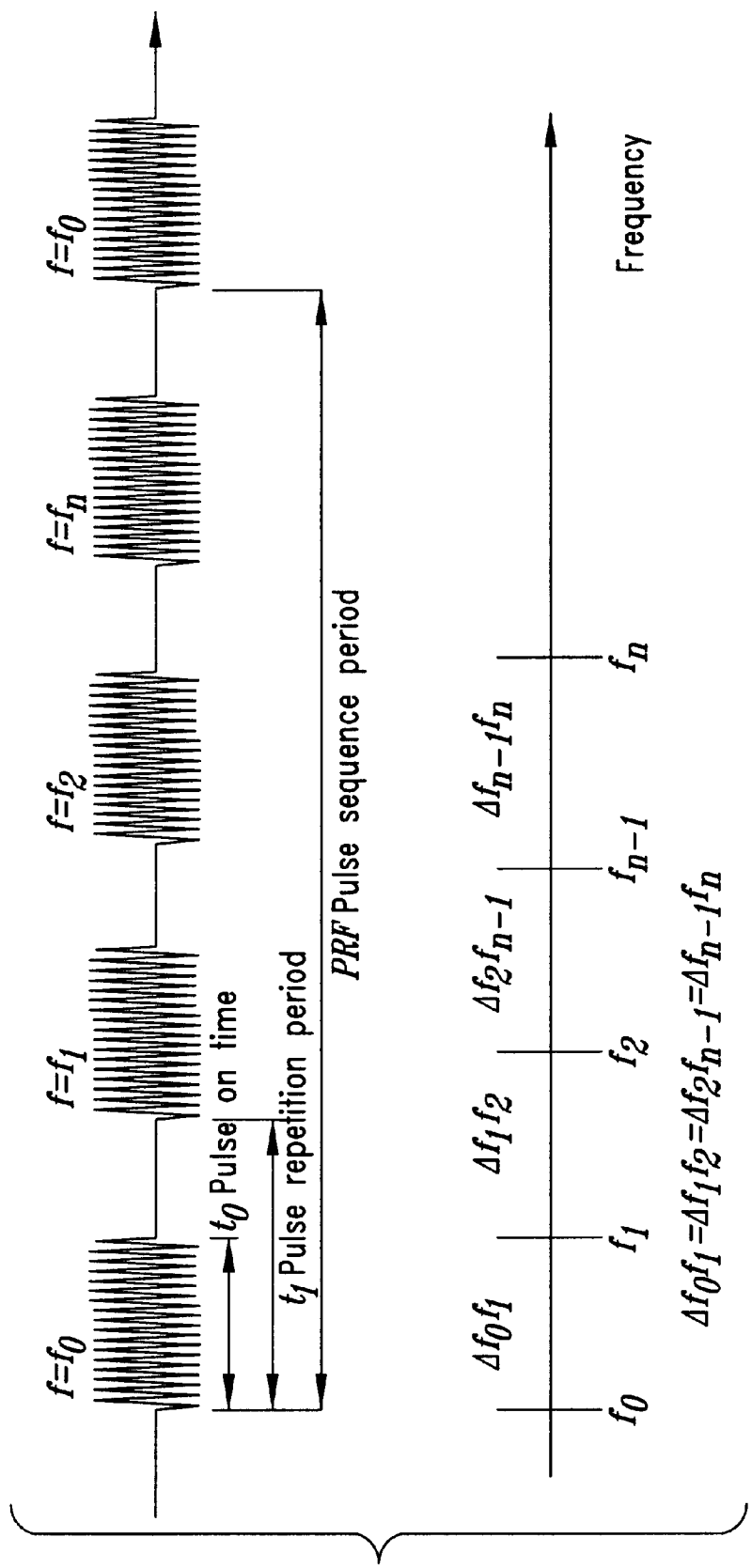
FIG. 9 shows multiple frequency pulses with multiple frequencies having equal spacing within the frequency domain and equal amplitude. This provides a less-sophisticated means for selecting multiple frequencies and may not necessarily result in improved image quality.
Figure 10:
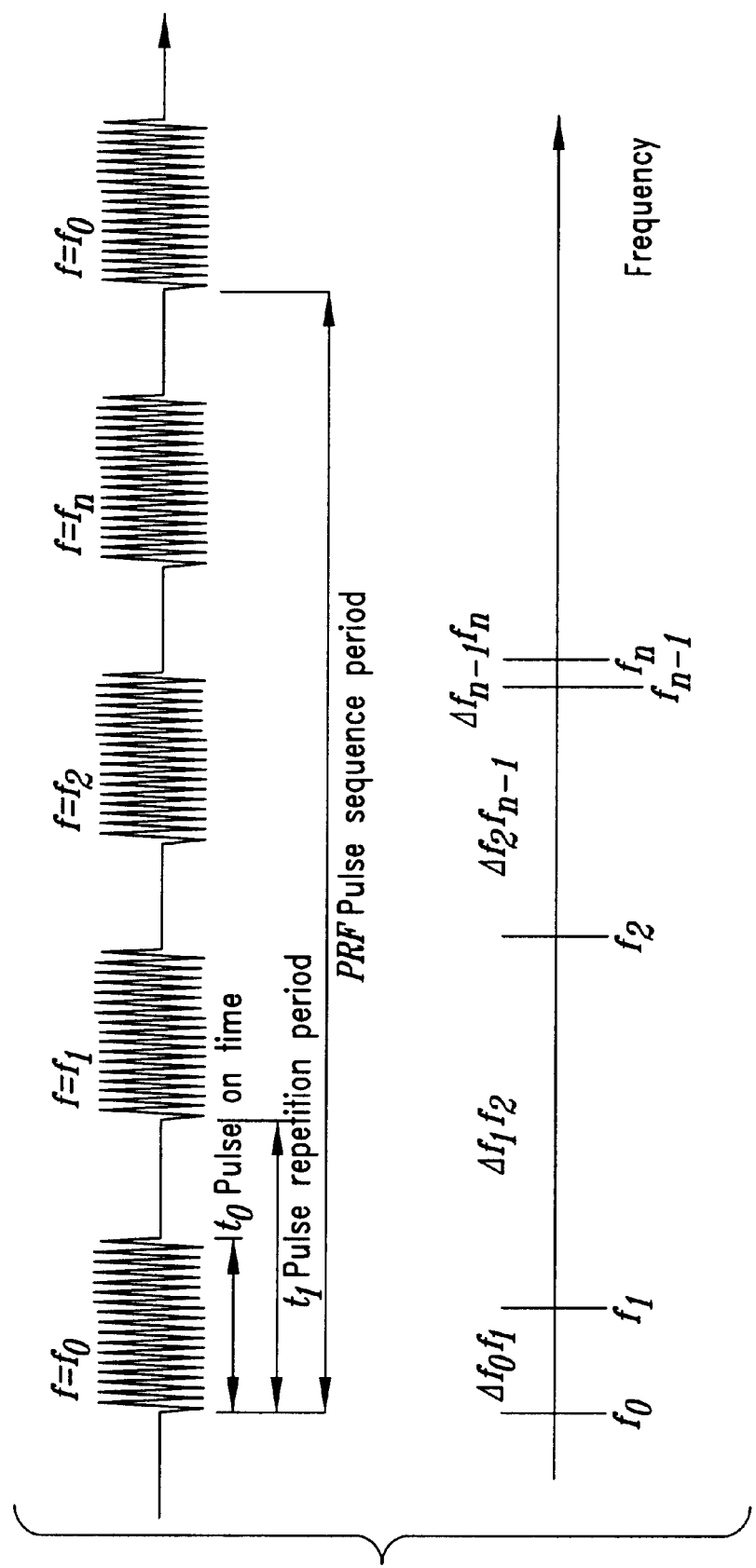
FIG. 10 shows the time line for multiple frequencies, however the frequencies are selected to provide the greatest enhancement of image information and are not necessarily equally spaced. The equation shows that the delta values (that is, frequency differences or spacing within frequency domain) are not equal. This process will allow the operating frequencies of the system to be specifically selected enhance image quality for a given type structure (e.g., cancerous tissue in the human breast).

In general, the present invention provides a process and an apparatus for generating multiple exposure ultrasonic holography images generated from a specific selected orientation each of which will insure multiple images, multiple intensities and multiple frequencies from each orientation. The process and the apparatus is designed for providing a multiple view, multiple angle insonification of the object such that the object sound intensity is of equal or near equal intensity across the entire field of the object. The process and the apparatus provide individual images at specific views and at specific intensities and frequency of sound to compare and analyze to achieve increased diagnostic value of the imaging process.

The present invention provides for multiple views of an object to be imaged with each view forming a separate hologram. Each separate hologram is constructed independently and at a rate (can be greater than 120 Hz) that is greater than the motion detection of the human eye (assumed to be approximately 30 Hz) and a rate required by a data acquisition apparatus (e.g., standard frame rate of CCD cameras). Thus, an averaging of "out of focus" contribution to the image is achieved to enhance the focusing capability of the acoustical holography process. There is an opportunity to have multiple of images that get collected into one composite image for viewing. This can be thought of in a similar manner as frame averaging but is different in that multiple images are combined into each "frame" of the output device. These multiple images then can be taken at multiple angular views to minimize the effect of "out of focal plane" structures. This process is the basis of U.S. Pat. No. 5,329,817 that provides an apparatus for multiple view images by either rotating the object transducer, making it "wobble" to achieve a multiple of off axis orientation, or by multiple pulsing individual transducers in a set array while the imaging process is underway.

The present invention provides a matrix of improvements to image quality, such as, providing for such "off axis" views to be electronically synched. From each selected view, one may arrange an apparatus that will provide the final image to be made up of only those selected views rather than at random angles. This will allow an operator to pre-select the preferred views from which to best see the structures of interest in the object and discriminate against others. Further, the apparatus provides a different ultrasound frequency to be used at each separate orientation or view, thus taking full advantage of not only the preferred orientation but also to improve the imaging of the subtle nature of structures, such as, edges and frequency sensitive soft tissue structures (tumor masses). In addition, the inventive apparatus allows for individual images to be formed at various frequencies with electronic compensation such that each frequency contribution is "equalized" such that all frequencies make a equal image intensity contribution to the composite final image.

A further disclosure provided herein is an apparatus that will provide for a different ultrasound intensity to be used at each separate orientation thus taking full advantage of not only the preferred orientation but also to improve the diagnostic value of the imaging process by differentiating the transmission characteristics of the subtle nature of structures (including, for example, entrapped air, bone, and cancerous tissue that each have different sound absorption and transmission characteristics). The inventive apparatus comprises multiple transducers on a rotating head or an oscillating assembly that can be rotated in a continuous motion while selecting specific orientations in which to make the holographic view or may be stopped at a preferred orientation and changed slightly by the operator to optimize the resulting view of the structure of the object of interest. As an example, three transducers (more or less) are orientated at 0, +5 and −5 degrees from the central axis of the acoustic path. Each of the transducers is sequentially used to perform subsequent images. This multiple transducer head is rotated and the image sequences synched such that preferred views are selected or held at a single orientation, controlled by the operator. This allows the operator to adjust the orientation for an optimum view while selecting the frequencies and sound intensity to be used for greatest diagnostic value of the image from the selected view.

Still a further improvement to the inventive apparatus is an "off acoustic axis" viewing angle that is adjusted. Such an adjustment process is selected in conjunction with the selection of the $f$Number. Moreover, the lens sharpens or expands the width of the focal plane. Thus, the apparatus will insonify the entirety of the object (to be viewed, such as breast tissue) at an equal or near equal sound intensity. One can also insonify selected portions of the object with greater intensity (e.g., near the chest wall when imaging a human breast). It should be noted that in human breast imaging, defining the location of the chest wall for purposes of orientation is of importance to the diagnostic process, because this portion of the anatomy has the greatest thickness and requires a greater amount of sound intensity than other portions of the breast.

View Orientation

The view orientation of the object to be imaged is synched to achieve an enhanced image of greater clarity and quality. While U.S. Pat. No. 5,329,817 achieved a multiple view to provide improved imaging in a selected focal plane of the object, the selection was random. A random selection proved to seldom be the preferred orientation. In other words, U.S. Pat. No. 5,329,817 described a process of having a large number of images (e.g., 120 per second) over the time frame of observation by the human eye or frame collection time of the recording camera (e.g., 30 frames per second). This process combined or averaged random orientations within a circular or wobble position of the object transducer. Although this averaging provided enhanced focal plane identification, the image information in the focal plane seldom was optimum due to a random orientation.

The present invention, by contrast, continues to provide an advantage of enhanced focal plane definition through multiple orientations and multiple views, but adds the key feature of being able to achieve multiple views from a non-random orientation that best illuminates and identifies the structure being imaged. For example, if one is primarily interested in imaging a tubular structure (e.g., a vein within the human body or a ductile structure of the female breast), the most informative view is achieved from multiple views with angles of orientation from the center line of the acoustic lens being in a plane that is perpendicular to the primary axis of the tubular structure.

Enhanced Image Information

The present invention provides for an enhanced image information of subtle structures from multiple frequency and multiple intensity imaging at a selected orientation. Taking sequential images at different frequencies enhances the image information and clarity. For example, combining separate images, each taken within a small time interval (e.g., 1/120 of a second), and each taken sequentially at one of several selected frequencies will significantly sharpen edge definition and smooth the grainy appearance of an image made with a coherent wave. There is image improvement as the number of frequencies and the range of frequencies is increased. The reason for this improvement is primarily for two reasons. First, the nature of holography requires that the image be formed with a single coherent sound source. However, making images with such coherent waves makes the image appear grainy due to the self-interference of the coherent wave. Combining several images at different frequencies smoothes out the appearance of the image and smoothly present greater levels of intensity referred to as gray scale. Secondly, there is an increased definition of edges and boundaries. This improvement results from the same considerations of needing many frequencies to successfully describe a sharp step boundary with a mathematical series of sine waves.

Previously, the orientation of view was not synchronized with the timing of the pulse of sound from the rotating object transducer source. Accordingly, the location at which a given image was taken became random as to rotational angle around the axis of rotation. This resulted in having multiple frequency images being taken at unpredictable orientations. Thus, there could occur images at one rotational angle being highly concentrated at one or two frequencies and being absent of contributions from other frequencies being used. The advantage of multiple frequency imaging was to use all of the sequence of frequencies within the range for each composite image taken but randomness compromised this advantage. The inventive process, by contrast, provides for the monitoring of the angular rotational position of the rotating transducer or the angular position of a wobbling transducer arrangement. A wobbling transducer is defined as one that is rotated in one dimension around an axis that is parallel to one of the centerlines of one dimension of the transducer face. By monitoring the rotation or wobble position of the source transducer, one can then control the start time of the image sound pulse and achieve a controlled view as well as a controlled frequency or intensity sequence within the selected view.

Combining Images

Each image is taken at sequential frequencies and with adjusted acoustic amplitude for equal image contribution. There is improved image quality from separately analyzing or combining images at discrete and separate frequencies. However, there is also an attenuation of sound through most objects that depends upon the frequency of the sound being used. That is, the higher the frequency of the sound the greater attenuation through the object (e.g., human tissue). Thus, in the operation U.S. Pat. No. 5,329,817, images from the lower frequencies made a brighter contribution to the composite image than those at higher frequencies. Also since there is a sequence of frequencies, that are repeated, this unbalanced contribution of frequencies causes the image contribution to flicker at the repetition rate of the overall sequence.

The present invention provides an electronic means of adjusting the amplitude of each energy pulse depending upon the frequency value and thus the attenuation of the sound at that frequency. This equalization of image contributions for each frequency allows the image to be constructed from a composite of images each of which makes equal contribution to the composite image and thus optimizes the improved affects of a smooth appearing image and one with sharper edge definition.

In U.S. Pat. No. 5,329,817 a method and apparatus is described that allows for multiple views of an object with a single transducer, wherein each view forms a separate hologram. Since these holograms are constructed independently and at rates (can be greater than 120 Hz) that are greater than the motion detection of the human eye (approximately 30 Hz) and the rate required by data acquisition apparatus (e.g., standard frame rate of CCD cameras) an averaging of "out-of-focus" contribution to the image is achieved to enhance the focusing capability of the acoustical holography process. Thus, there is an opportunity to have multiple of images that get collected into one composite image for viewing. This can be thought of in a similar manner as frame averaging but is different in that multiple images are combined into each "frame" of the output device. These multiple images then can be taken at multiple angular views to minimize the effect of "out-of-focal plane" structures. Thus, U.S. Pat. No. 5,329,817 discloses an apparatus that will obtain multiple view images by either rotating a transducer, making a single transducer "wobble" to achieve a multiple of off-axis orientations, or using a multiple pulsing single transducer in a set order while the imaging process is underway.

Choice of Imaging Parameters

The present invention, essentially, provides a matrix of various variable parameters of ultrasonic pulsed wave transmission. The choice and selection of each of the multiple parameters depends entirely of the nature of the object to be imaged. For example, to image bone tissue in the presence of soft structure, a person skilled in this art will use a lower frequency (e.g., 1–2 MHz) and a higher amplitude because the lower frequency is less attenuated. Moreover, bone tissue has much greater attenuation than the surrounding soft tissue. Similarly, subtle soft tissue structures (e.g., tumor masses) will provide information if taken at higher frequencies (e.g., 3–10 MHz) to show subtle structures of soft tissue. One skilled in the art will benefit by having the option of taking images at selected amplitudes and specifically selected frequencies to best achieve image information quality and information of the tissue at interest. Moreover, the ability to combine into one image, multiple images taken at different frequencies and amplitude provides greater image information than each separate image.

It should be noted that frequency and amplitude parameters can be adjusted during an imaging process, such as when an object to be studied in more detail is noticed. In such a situation, for example, the field can be enlarged or "zoomed" into the object to be studied and the frequency and amplitude adjusted to correspond to the optimal parameters of this newly enlarged field. For example, if bone tissue is present in a "wide angle" image, the frequency of a zoomed in image can be altered to account for the type of information to be obtained and the presence or absence of harder bone tissue within the zoomed image.

Amplitude, a used herein, refers to the intensity of the energy provided within a pulse wave of acoustic holography.

In summary, one aspect of the present invention is to allow off-axis views to be electronically "synched" such that from each selected view one may arrange apparatus that will provide the final image to be made up of only those selected views rather than at random angles. The many advantages provided include the ability of an operator to pre-select the preferred views from which to best see the internal structures of interest in the object and discriminate against others that might detract from the image.

The inventive apparatus enables a different ultrasonic energy to be used at each separate orientation. This provides a process to take full advantage of not only the preferred orientation but also to improve the imaging of the subtle nature of structures, such as edges and frequency sensitive soft tissue structures. This further allows individual images to be formed at various frequencies with electronic compensation such that each frequency contribution is "equalized" such that all frequency make a equal image intensity contribution to the composite final image. When a different ultrasound intensity is used at each separate orientation, the diagnostic value of the imaging process improves by differentiating the transmission characteristics of the subtle nature of structures e.g., entrapped air, bone, cancerous tissue which have different sound absorption and transmission characteristics.

The inventive apparatus provides for multiple transducers on a rotating head that are allowed to rotate in a continuous motion while selecting specific orientations in which to make the holographic view or are stopped at a preferred orientation and changed slightly by the operator to optimize the resulting view of the structure of the object of interest. For example, three (more or less) could be orientated at 0, +5 and −5 degrees from the central axis of the acoustic path. Each of the transducers are then sequentially used to perform subsequent images. This head is rotated and the image sequences synched such that preferred views are selected or are held at a single orientation, which is controlled by the operator. This allows the operator to adjust the orientation for an optimum view while selecting the frequencies and sound intensity to be used for greatest diagnostic value of the image from the selected view.

The inventive apparatus allows an "off acoustic axis" viewing angle to be adjusted. Such a process is selected in conjunction with the selection of the ƒNumber of the lens to sharpen or expand the width of the focal plane. Moreover, the apparatus will intensify the entirety of the object at an equal or near equal sound intensity. A modification is to intensify selected portions of the object with greater intensity, such as, near the chest wall when imaging a human breast. It should be noted that in applications to human breast imaging, defining the location of the chest wall for purposes of orientation is of importance to the diagnostic process. This portion of the anatomy has the greatest thickness and thus requires a greater amount of sound intensity than other portions of the breast.

We claim:

1. A process for improving image quality in an ultrasonic imaging apparatus, wherein the ultrasonic imaging apparatus comprises a transducer assembly, a transducer means having one or more transducers for outputting an ultrasonic wave, an acoustic lens assembly, and a holographic image detection system, and a transducer assembly electric control means for controlling frequency, power, timing and duration of ultrasonic output pulse, spherical or cylindrical waves of the transducer means wherein the transducer means is mounted on a movable support having a center axis, comprising the steps of:

(a) providing an object to be internally imaged to be held by the object holder;

(b) transmitting a pulse sequence of ultrasound, each pulse within the sequence comprises a plurality of cycles of a single frequency (ƒ) of ultrasound, wherein each sequence comprises multiple frequency pulses ($f_1, f_2, f_3, \ldots f_n$); and (c) imaging the object from a hologram formed in the holographic detection system for each pulse within the sequence.

2. The process for improving image quality of claim 1 wherein the process further comprises either capturing each separate image for separate analysis for a specific frequency, or averaging a plurality of images from selected frequencies to form a composite image derived from the selected frequencies.

3. The process for improving image quality of claim 2 wherein the imaging technique utilizes an apparatus having an acoustically opaque element selectively positioned at the focal point of the ultrasonic energy that is not scattered by the object to prevent only to pass only transmission of ultrasonic energy directed to the focal point, thus providing either a dark background image or a white background image respectively.

4. The process for improving image quality of claim 3 wherein the acoustically opaque element is made from an acoustical insulating material having entrapped voids or air.

5. The process for improving image quality of claim 4 wherein the acoustical insulating material is selected from the group consisting of cork, porous polymers, open or closed cell foams, and combinations thereof.

6. The process for improving image quality of claim 1 wherein the transmitting the pulse sequence of multiple frequencies chooses the frequencies to have equal incremental increases of each frequency.

7. The process for improving image quality of claim 1 wherein the transducer means transmits each pulse sequence of ultrasound at a single acute incidence angle (θ) or at multiple acute incidence angles ($\theta_1, \theta_2, \theta_3, \ldots \theta_n$).

8. The process for improving image quality of claim 1 wherein the transducer means transmits each pulse sequence of ultrasound at a single amplitude or at multiple amplitudes ($A_1, A_2, A_3, \ldots A_n$).

9. The process for improving image quality of claim 8 wherein the process further comprises either capturing each separate image for separate analysis for a specific frequency, or averaging a plurality of images from selected frequencies to form a composite image derived from the selected frequencies.

10. An ultrasonic imaging apparatus for improving ultrasonic holography image quality comprising:

a transducer assembly;

an object holder surrounded by acoustically transmissive media, an acoustic lens assembly, and a holographic image detection system;

a transducer assembly electric control means for controlling frequency, power, timing and duration of an ultrasonic output pulse, and a transducer, wherein the transducer is mounted on a movable support having a center axis, and wherein the transducer assembly transmits a pulse sequence of ultrasound, wherein each pulse within the sequence comprises a plurality of cycles of a single frequency (ƒ) of ultrasound, wherein each sequence comprises multiple frequency pulses ($f_1, f_2, f_3, \ldots f_n$).

11. The ultrasonic imaging apparatus for improving ultrasonic holography image quality of claim 10 wherein the apparatus further comprises an image analysis assembly that either captures each separate image for separate analysis for a specific frequency, or averages a plurality of images from selected frequencies to form a composite image derived from the selected frequencies.

12. The ultrasonic imaging apparatus for improving ultrasonic holography image quality of claim 11 wherein the imaging technique utilizes an apparatus having an acoustically opaque element selectively positioned at the focal point to prevent only or pass only transmission of ultrasonic energy directed to the focal point.

13. The ultrasonic imaging apparatus for improving ultrasonic holography image quality of claim 12 wherein the acoustically opaque element is made from an acoustical insulating material having entrapped voids or air.

14. The ultrasonic imaging apparatus for improving ultrasonic holography image quality of claim 13 wherein the acoustical insulating material is selected from the group consisting of cork, porous polymers, open or closed cell foams, and combinations thereof.

15. The ultrasonic imaging apparatus for improving ultrasonic holography image quality of claim 10 wherein the transducer assembly transmits a sequence of pulses, each pulse being a different frequency and chooses the frequencies to have equal incremental increases of each frequency.

16. The ultrasonic imaging apparatus for improving ultrasonic holography image quality of claim 10 wherein the transducer transmits each pulse sequence at a single acute incidence angle (θ) or at multiple acute incidence angles ($\theta_1, \theta_2, \theta_3, \ldots \theta_n$).

17. The ultrasonic imaging apparatus for improving ultrasonic holography image quality of claim 10 wherein the transducer transmits each pulse sequence of ultrasound at a single amplitude (power, A) or at multiple amplitudes ($A_1, A_2, A_3, \ldots A_n$).

18. An ultrasonic imaging apparatus for improving ultrasonic holography image quality comprising:
   a transducer assembly;
   an acoustic lens assembly;
   a holographic image detection system;
   a transducer assembly electric control means for controlling frequency, power, timing and duration of an ultrasonic output pulse;
   a plurality of a transducer elements for transmission of ultrasound, wherein the transducer elements are mounted on a movable support having a center axis movable at an angle of incidence ($\theta$), and wherein the transducer assembly transmits a pulse sequence of ultrasound, wherein each pulse within the sequence comprises a plurality of cycles of a single frequency ($f$) of ultrasound, wherein each sequence is composed of a plurality of distinct pulses comprises a single or multiple frequency pulses ($f_1, f_2, f_3, \ldots f_n$).

19. The ultrasonic imaging apparatus for improving ultrasonic holography image quality of claim 18 wherein the apparatus further comprises and image analysis assembly that either captures each separate image for separate analysis for a specific frequency, or averages a plurality of images from selected frequencies to form a composite image derived from the selected frequencies.

20. The ultrasonic imaging apparatus for improving ultrasonic holography image quality of claim 19 wherein the imaging technique utilizes an apparatus having an acoustically opaque element selectively positioned at the focal point to prevent transmission of ultrasonic energy directed to the focal point to provide for a dark image.

21. The ultrasonic imaging apparatus for improving ultrasonic holography image quality of claim 20 wherein the acoustically opaque element is made from an acoustical insulating material having entrapped voids or air.

22. The apparatus according to claim 18 further including a reference sequence of pulses and wherein each pulse in the reference sequence is at the same frequency.

23. The apparatus according to claim 18 wherein each pulse in the sequence is at a different frequency than every other pulse in the same sequence.

24. The ultrasonic imaging apparatus for improving ultrasonic holography image quality of claim 18 wherein the transducer elements transmit each pulse sequence of ultrasound at a single amplitude (power, A) or at multiple amplitudes ($A_1, A_2, A_3, \ldots A_n$).

25. A process for improving image quality in an ultrasonic imaging apparatus, wherein the ultrasonic imaging apparatus comprises a transducer assembly;
   an acoustic lens assembly;
   a holographic image detection system; a transducer assembly electric control means for controlling frequency, power, timing and duration of an ultrasonic output pulse;
   and a transducer, wherein the transducer is mounted on a movable support having a center axis, comprising the steps of:
     (a) providing an object to be internally imaged to be held by the object holder;
     (b) transmitting a pulse sequence of ultrasound, each pulse within the sequence comprises a plurality of cycles and each pulse within the sequence has a different amplitude then every other pulse in the sequence and
     (c) imaging the object from a hologram formed in the holographic detection system for each pulse within the sequence.

26. The process for improving image quality in an ultrasonic imaging apparatus quality of claim 25 wherein the process further comprises either capturing each separate image for separate analysis for a specific frequency, or averaging a plurality of images from selected frequencies to form a composite image derived from the selected frequencies.

27. The process for improving image quality in an ultrasonic imaging apparatus quality of claim 26 wherein the imaging technique utilizes an apparatus having an acoustically opaque element selectively positioned at the focal point to prevent transmission of ultrasonic energy directed to the focal point to provide for a dark image.

28. The process for improving image quality in an ultrasonic imaging apparatus quality of claim 27 wherein the acoustically opaque element is made from an acoustical insulating material having entrapped voids or air.

29. The process for improving image quality in an ultrasonic imaging apparatus quality of claim 25 wherein the transmitting the pulse sequence of multiple frequencies chooses the frequencies to have equal incremental increases of each frequency.

30. The process for improving image quality in an ultrasonic imaging apparatus quality of claim 25 wherein the transducer transmits each pulse in the sequence of ultrasound at a single acute incidence angle ($\theta$) or at multiple acute incidence angles ($\theta_1, \theta_2, \theta_3, \ldots \theta_n$).

31. An ultrasonic imaging apparatus for improving ultrasonic holography image quality comprising:
   a transducer assembly;
   an acoustic lens assembly, a holographic image detection system;
   a transducer assembly electric control means for controlling frequency, power, timing and duration of ultrasonic output pulse; and
   a transducer element for transmission of ultrasound, wherein the transducer element is mounted on a movable support having a center axis movable at an angle of incidence ($\theta$), and wherein the transducer assembly transmits a pulse sequence of ultrasound, wherein each pulse within the sequence comprises a plurality of cycles of ultrasound, wherein each sequence comprises a single or multiple frequency pulses ($f_1, f_2, f_3, \ldots f_n$) and multiple amplitudes ($A_1, A_2, A_3, \ldots A_n$).

32. The ultrasonic imaging apparatus of claim 31 wherein the apparatus further comprises an image analysis assembly that either captures each separate image for separate analysis for a specific frequency, or averages a plurality of images from selected frequencies to form a composite image derived from the selected frequencies.

33. The ultrasonic imaging apparatus of claim 32 wherein the imaging technique utilizes an apparatus having an acoustically opaque element selectively positioned at the focal point to prevent only or pass only transmission of ultrasonic energy directed to the focal point to provide for a dark image.

34. The ultrasonic imaging apparatus of claim 33 wherein the acoustically opaque element is made from an acoustical insulating material having entrapped voids or air.

35. An apparatus comprising:
   a transducer assembly means for generating an acoustic signal to pass through an object;
   a lens means for receiving an acoustic signal after it has passed through the object;
   a holographic image detection means for receiving the acoustic signal after it has passed through the lens; and electronic control means for causing the transducer assembly means to generate a plurality of pulses spaced from each other in time, the plurality of pulses forming a sequence of pulses, each pulse having a selected frequency within the pulse itself and plurality of the pulses in the sequence having a different frequency from each other.

36. The apparatus of claim 35 wherein a plurality of the pulses in the sequence have a different amplitude from each other.

37. The apparatus of claim 35 wherein the frequency difference between a first pulse and a second pulse within the plurality of pulses of a sequence is the same as the frequency difference between the second pulse and a third pulse of the same sequence.

38. The apparatus of claim 35 wherein the frequency difference between a first pulse and a second pulse within the plurality of pulses of a sequence is different than the frequency difference between the second pulse and a third pulse of the same sequence.

39. A method generating an acoustic hologram comprising:

generating a plurality of acoustic pulses;

transmitting the plurality of acoustic pulses as a sequence of pulses through an object;

varying a property of the acoustic pulse from one pulse to another pulse within the sequence of pulses passing through the object;

receiving the sequence of pulses that have passed through the object; and creating an image for each pulse in the sequence that contains varying data based on the property of the pulse that was varied.

40. The method according to claim 39 in which the property varied from one pulse to another is the frequency of the acoustic wave of the pulse, each pulse being at a single acoustic frequency itself but at a different acoustic frequency from another pulse in the same sequence.

41. The method according to claim 39 in which the property varied from one pulse to another pulse is the amplitude of the acoustic wave of the pulse, each pulse being at a different amplitude from another pulse in the same sequencer.

42. The method according to claim 39 further including:

rotating a source of the acoustic pulses during generation of the sequence of acoustic pulses;

varying the point within the angle of rotation of the generation of the acoustic pulse from one pulse to another pulse within the sequence of pulses in order to vary the property of the acoustic pulse from one pulse to another within the sequence of pulses.

43. The method according to claim 42 further including:

transmitting each pulse at a different rotational position during the generation of the plurality of the acoustic pulses.

44. The method according to claim 42 further including:

generating each pulse of the plurality of the acoustic pulses at the same rotational position for each pulse in the sequence.

45. The method according to claim 40 wherein the difference in frequency from one pulse to another pulse is the same as the difference in frequency for each pulse within the sequence.

46. The method according to claim 40 wherein the difference in frequency from one pulse to a second pulse is different than the difference in frequency between any other two pulses within the sequence.

47. The method according to claim 40 wherein the difference in frequency between a first pulse and a second pulse within the sequence is different than the difference in frequency between a second pulse and a third pulse in the same sequence.

48. The method according to claim 40 wherein the difference in frequency between a first pulse in the sequence and the second pulse in the sequence is the same as the difference in frequency between the second pulse of the sequence and a third pulse in the same sequence.

* * * * *